United States Patent
Hoogenakker et al.

(10) Patent No.: US 9,265,550 B1
(45) Date of Patent: Feb. 23, 2016

(54) DEVICE AND METHOD FOR REMOVING GAS FROM A MIXTURE OF BIOMATERIALS

(71) Applicant: Nordson Corporation, Westlake, OH (US)

(72) Inventors: Jon E. Hoogenakker, Inver Grove Heights, MN (US); Huadong Lou, Plymouth, MN (US); Bradley D. Robb, Maple Plain, MN (US)

(73) Assignee: NORDSON CORPORATION, Westlake, OH (US)

( * ) Notice: Subject to any disclaimer, the term of this patent is extended or adjusted under 35 U.S.C. 154(b) by 0 days.

(21) Appl. No.: 14/920,761

(22) Filed: Oct. 22, 2015

Related U.S. Application Data (62) Division of application No. 14/196,595, filed on Mar. 4, 2014, now Pat. No. 9,174,147.

(60) Provisional application No. 61/772,849, filed on Mar. 5, 2013.

(51) Int. Cl.
  *A61B 17/88* (2006.01)
  *B01D 19/00* (2006.01)

(52) U.S. Cl.
  CPC ........ *A61B 17/8827* (2013.01); *B01D 19/0036* (2013.01); *B01D 19/0063* (2013.01)

(58) Field of Classification Search
  CPC combination set(s) only.
  See application file for complete search history.

(56) References Cited

U.S. PATENT DOCUMENTS

| | | | |
|---|---|---|---|
| 4,287,819 A | 9/1981 | Emerit | |
| 5,779,356 A | 7/1998 | Chan | |
| 6,045,555 A | 4/2000 | Smith et al. | |
| 7,393,342 B2 | 7/2008 | Henniges et al. | |
| 7,670,384 B2 | 3/2010 | Kumar et al. | |
| 7,927,563 B1 | 4/2011 | Lavi | |
| 8,118,813 B2 | 2/2012 | Perez-Cruet et al. | |
| 8,439,929 B1 | 5/2013 | Sharratt et al. | |
| 2008/0214998 A1 | 9/2008 | Kurek et al. | |
| 2012/0330229 A1 | 12/2012 | Greter | |
| 2014/0098629 A1 | 4/2014 | Greter | |

OTHER PUBLICATIONS

Nordson Corporation, OsteoXpress™ Bone Graft Delivery, www.nordson.com/en-us/divisions/micromedics/products/bone-graft-delivery/pages/default.aspx, 1 pg., 2013.
MEDMIX Systems AG, Bone-Graft Delivery System, Brochure, 4 pgs., undated.

*Primary Examiner* — Duane Smith
*Assistant Examiner* — Adam W Bergfelder
(74) *Attorney, Agent, or Firm* — Baker & Hostetler LLP (57) ABSTRACT

A device and method for removing gas from a mixture of biomaterials includes a vacuum pump movably positioned within a cavity of a syringe at least partially defining a vacuum chamber. The vacuum pump has a pump body with proximal and distal portions, a stopper connected to the distal portion, and a flow channel. The stopper includes an inlet, and the pump body includes a port. The flow channel extends from the inlet to the port and is in fluid communication with the vacuum chamber. A first valve is positioned within the flow channel between the inlet and the port. The first valve is operable to open and close the flow channel for selectively connecting a vacuum to the vacuum chamber such that gas is withdrawn from mixture of biomaterials within the vacuum chamber.

7 Claims, 8 Drawing Sheets

DEVICE AND METHOD FOR REMOVING GAS FROM A MIXTURE OF BIOMATERIALS

CROSS-REFERENCE TO RELATED APPLICATION

This application is a divisional of application Ser. No. 14/196,595, filed Mar. 4, 2014, which is a non-provisional of Application Ser. No. 61/772,849, filed Mar. 5, 2013, the disclosures of which are hereby incorporated by reference herein.

TECHNICAL FIELD

The present invention relates generally to a device and method for removing gas from a mixture of biomaterials, and more particularly, to a device and method for removing gas from a bone graft material.

BACKGROUND

Bone grafting is a surgical procedure for repairing bones and typically involves introducing a mixture of particulate, such as bone graft material, into an area of bone that requires repair, such as a fracture. The bone graft material is intended to stimulate growth of healthy native bone tissue, and new native bone tissue may eventually replace the bone graft material completely. Bone graft material is a type of biomaterial and typically includes a combination of crushed bone and a liquid component, such as blood, plasma, or growth factors. Bone graft materials can be allograft (derived from a human other than the one receiving the graft), autograft (derived from the human receiving the graft), and synthetic (created from, for example, ceramics like calcium phosphates).

Bone graft materials are typically delivered to a surgical site using syringe-like delivery devices, which often include attachments, such as small diameter cannulae. In addition, the components of the bone graft material are sometimes brought together and combined to form the mixture of the bone graft material in the delivery device. However, the mixture of the bone graft material tends to also include gas from the porosity of the crushed bone and the aeration associated with mixing the components. As the bone graft materials dry after being applied to the surgical site, a portion of the gas collects into pockets within the setting bone graft material. The pockets create inconsistencies in the final bone graft material that may result in performance variation throughout the bone graft material.

There is a need for a device and method for removing gas from a mixture of biomaterials, such as a mixture of bone graft materials, that reduces the gas within the mixture and addresses present challenges and characteristics such as those discussed above.

SUMMARY

An exemplary embodiment of a device for removing a gas from a mixture of biomaterials includes a syringe and a vacuum pump. The syringe has a syringe body and a cavity within the syringe body. The syringe body has a proximal opening and a distal opening. The vacuum pump is movably positioned within the cavity such that the vacuum pump and syringe body at least partially define a vacuum chamber. In addition, the vacuum pump is received by the proximal opening and movable toward the distal opening for discharging the mixture of biomaterials from the distal opening.

The vacuum pump includes a pump body, a stopper, a flow channel, and first valve. The pump body has a proximal portion and a distal portion. The distal portion includes a port configured to operatively engage a vacuum device for generating a vacuum therein. The stopper has an inlet and is operatively connected to the distal portion of the pump body. The flow channel extends from the inlet to the port such that the stopper, the pump body, and the vacuum chamber are in fluid communication. As such, the flow channel is adapted to fluidly connect the vacuum and the vacuum chamber.

The first valve is positioned between the inlet and portion within the flow channel. The first valve is also operable to open and close the flow channel for selectively connected the vacuum to the vacuum chamber. Accordingly, the vacuum within the vacuum device withdraws gas from the mixture of biomaterials within the vacuum chamber.

In use, gas is removed from the mixture of biomaterials by generating a vacuum through the flow channel in fluid communication with the vacuum chamber. The method also includes withdrawing the gas through the flow channel within the stopper and removing the gas from the mixture of biomaterials within the vacuum chamber.

In one aspect, the method further includes opening a valve to fluidly connect the flow channel to the vacuum chamber. In addition, the mixture of biomaterials may include a particulate and a liquid so that the method also includes hydrating the particulate with the liquid by withdrawing gas from the vacuum chamber.

Various additional objectives, advantages, and features of the invention will be appreciated from a review of the following detailed description of the illustrative embodiments taken in conjunction with the accompanying drawings.

BRIEF DESCRIPTION OF THE DRAWINGS

The accompanying drawings, which are incorporated in and constitute a part of this specification, illustrate embodiments of the invention and, together with a general description of the invention given above, and the detailed description given below serve to explain the invention.

DETAILED DESCRIPTION

Figure 1:
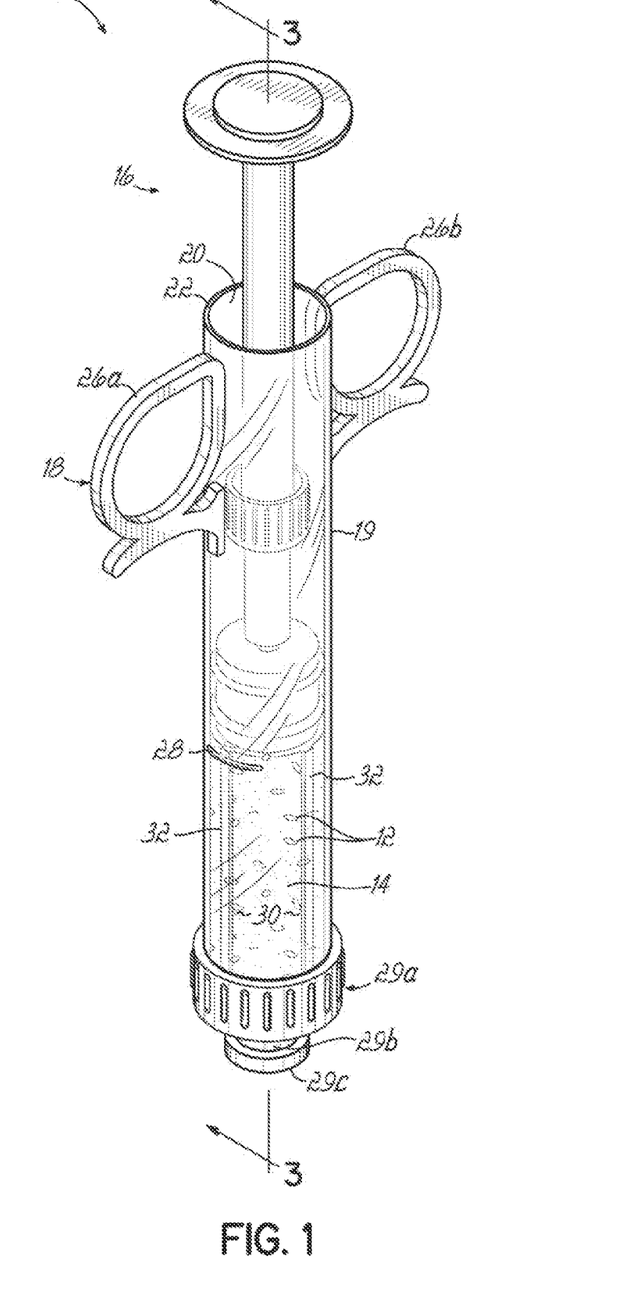
FIG. 1 is a perspective view of an embodiment of a device for removing a gas from a mixture of bone graft material.

With reference to FIG. 1, an embodiment of a device 10 for removing a gas 12 from a mixture 14 of biomaterials includes a vacuum pump 16 positioned within a syringe 18. Generally, the mixture 14 of biomaterials, also referred to below as the mixture 14, may be any combination of biomaterial components, such as dry particulate and/or liquid components. However, according to an exemplary embodiment, the mixture 14 of biomaterials is a bone graft material. The syringe 18 has a generally cylindrical syringe body 19 having a cavity 20 extending therethrough. The syringe 18 also includes a proximal opening 22 and a distal opening 24 (see FIG. 3). The vacuum pump 16 is positioned at least partially within the cavity 20 through the proximal opening 22. The distal opening 24 (see FIG. 3) is positioned opposite from the proximal opening 22 and receives the mixture 14. In addition, the syringe 18 includes a pair of finger grips 26a, 26b projecting outwardly from the syringe body 19 away from the cavity 20 for providing additional grip for manipulation of the device 10 by a practitioner, such as a doctor, nurse, or similarly trained medical professional. With respect to the use of the terms "distal" and "proximal," it will be appreciated that such directions are intended to describe relative locations along exemplary embodiments of the device 10. It is not intended that the terms "distal" and "proximal" limit the invention to any of the exemplary embodiments described herein.

Generally, the vacuum pump 16 may be inserted to any desirable position within the cavity 20. However, an exemplary embodiment of the syringe 18 has a max fill line 28, or other visual indicia, for indicating a desirable placement of the vacuum pump 16 within the cavity 20. The syringe body 19 is also transparent for viewing the mixture 14 within the cavity 20 and properly positioning the vacuum pump 16. Of course, it will be appreciated that the syringe 18 may alternatively be translucent for viewing the contents therein. Furthermore, an end cap 29a is removably attached to the syringe body 19 to cover and fluidly seal the distal opening 24 (see FIG. 3). In this respect, the vacuum pump 16, the syringe body 19, and the end cap 29a define a vacuum chamber 30 into which the mixture 14 is placed for removing the gas 12 therein. The end cap 29a is threaded onto the syringe body 19 and further includes a coupling, which may be in the form of a male luer coupling 29b and female luer cap 29c. The syringe body 19 also includes a plurality of grooves 32 extending between the max fill line 28 and the distal opening 24. The plurality of grooves 32 further define the vacuum chamber 30 and collect gas under the influence of the vacuum, the use of which will be described below in greater detail. Specifically, each of the plurality of grooves 32 is generally 0.001 inches deep within the syringe body 19. In the alternative, the end cap 29a may be used with or replaced by other accessories. As such, the vacuum chamber 30 may vary in accordance with the structures of these accessories, which will also be described below in greater detail. According to the exemplary embodiment, the device 10 receives approximately 5 cc of the mixture 14. However, it will be appreciated that the device 10 may also be configured for receiving 1 cc of mixture or any other volume of mixture 14 desirable for use by the practitioner in accordance with the principles of the invention described herein.

Figure 2:
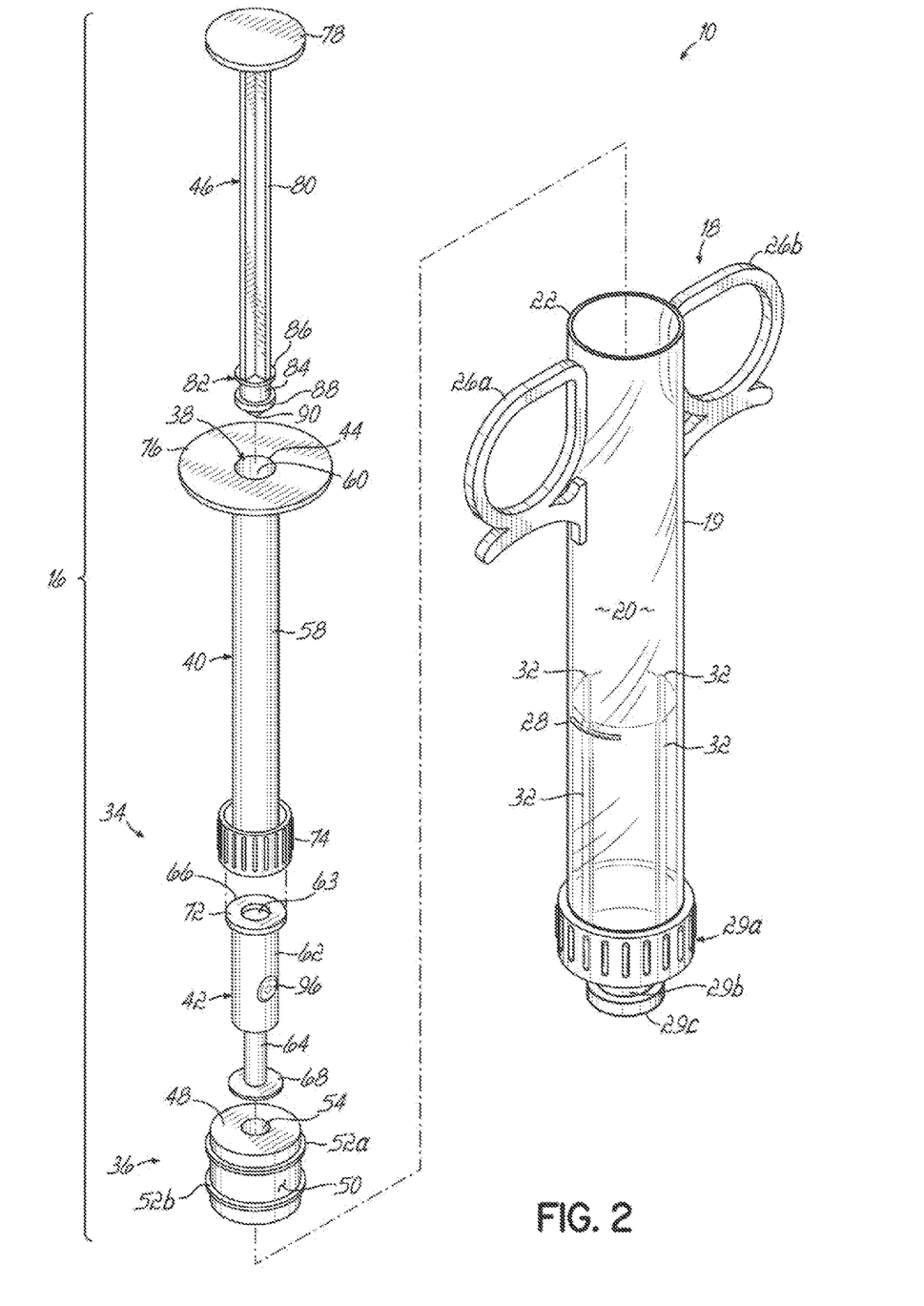
FIG. 2 is an exploded view of the device of FIG. 1.
Figure 3:
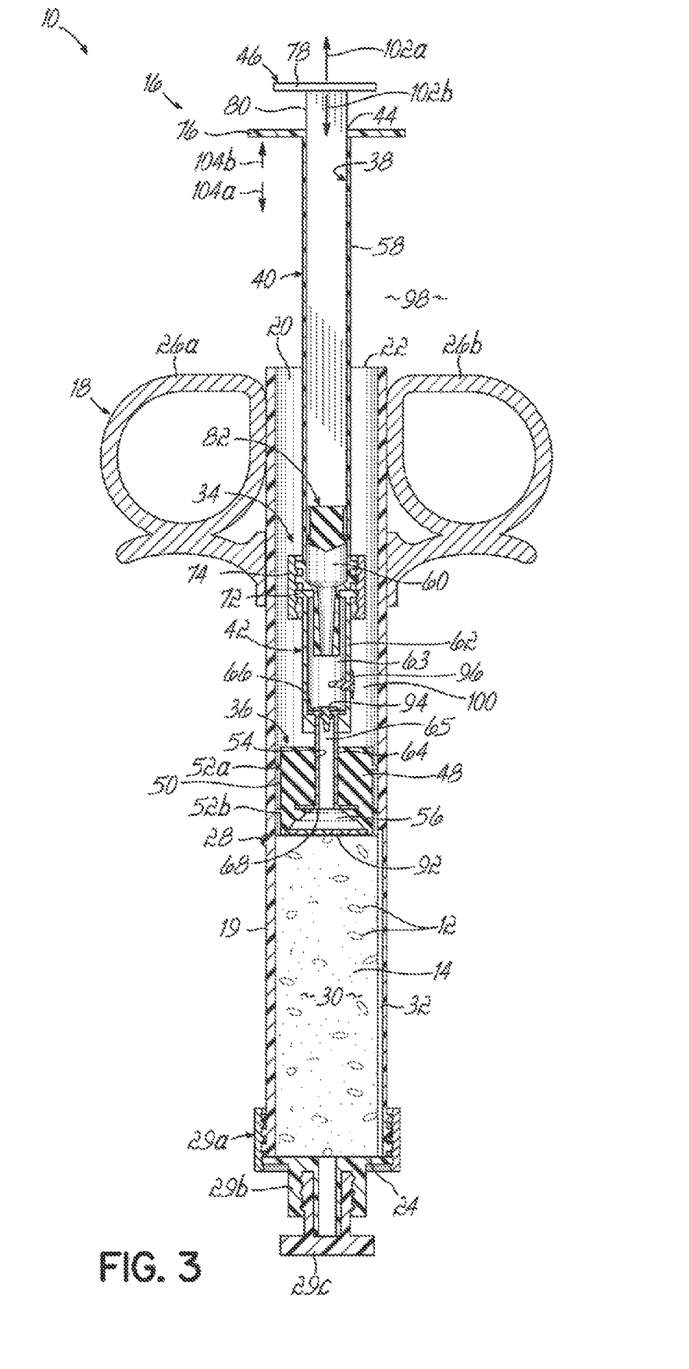
FIG. 3 is a cross-section view of FIG. 1 taken along section line 3-3.

As shown in FIG. 2 and FIG. 3, the vacuum pump 16 includes a pump body 34, a stopper 36 operatively connected to the pump body 34, and a flow channel 38 extending through the pump body 34 and stopper 36. The pump body 34 includes a proximal portion 40 and a distal portion 42. The distal portion 42 is connected to the stopper 36. The proximal portion 40 includes a port 44 configured to operatively engage a vacuum device for generating a vacuum within the flow channel 38. According to an exemplary embodiment, the vacuum device is a vacuum plunger 46. The vacuum plunger 46 is received by the port 44 and movably positioned within the flow channel 38 for generating the vacuum therein.

The stopper 36 generally includes a barrel shaped stopper body 48 having an outer surface 50 configured for fluidly sealing against the syringe body 19 within the cavity 20. More particularly, the outer surface 50 includes a pair of circumferential stopper seals 52a, 52b. Each of the stopper seals 52a, 52b seals against the syringe body 19 within the cavity 20 to prevent fluid from passing by the stopper seals 52a, 52b but also permits distal and proximal movement of the stopper 36 along the cavity 20. The stopper 36 also has a hole 54 extending through the stopper body 48 to an inlet 56. According to the exemplary embodiment, the stopper 36 is formed from an elastomeric material, such as rubber, for improving sealing and movement within the syringe body 19.

As briefly described above, the pump body 34 includes the proximal portion 40 and the distal portion 42. More particularly, the proximal portion 40 includes a cylinder body 58 defining a bore 60, and the distal portion 42 includes a valve support body 62 defining a passage 63 and a stem 64 defining a conduit 65. Generally, the valve support body 62 is operatively connected to the stopper 36 via the stem 64. The stem 64 has a proximal end 66 and a distal lip 68 with the conduit 65 extending through each. The proximal end 66 of the stem 64 is connected to the valve support body 62 such that the stem 64 projects distally from the valve support body 62 toward the stopper 36. In contrast, the stem 64 is inserted within the hole 54 of the stopper 36 so that the distal lip 68 cooperates with the elastomeric stopper 36 to affix the valve support body 62 relative to the stopper 36. In fact, the stem 64 extends into the hole 54 of the stopper 36 far enough to fluidly connect the conduit 65 of the stem 64 between the passage 63 of the valve support body 62 and the inlet 56 of the stopper 36.

Furthermore, the proximal portion 40 of the pump body 34 is separable from the distal portion 42. In this respect, a first female luer lock 72 is proximally positioned on the valve support body 62 and removably couples with a first male luer lock 74 distally positioned on the proximal portion 40 of the pump body 34. When the first female and male luer locks 72, 74 couple together, the bore 60 of the cylinder body 58 fluidly connects to the passage 63 of the valve support body 62. Proximal from the first male luer lock 74, the pump body 34 also includes a handgrip 76 connected to the cylinder body 58 adjacent to the port 44. More particularly, the handgrip 76 of the exemplary embodiment, is generally circular, planar, and surrounds the port 44. Notably, the handgrip 76 is positioned along the pump body 34 for improving manipulation of the vacuum pump 16 during use. As such, the handgrip 76 is generally larger than the cavity 20 of the syringe body 19, while the remainder of the vacuum pump 16 distal from the handgrip 76 is sized for insertion within the syringe body 19. Because of this respective size, the handgrip 76 will abut the syringe body 19 adjacent to the proximal opening 22 for preventing the vacuum pump 16 from falling through the distal opening 24 of the syringe body 19.

Finally, the vacuum plunger 46 is configured for being movably inserted within the bore 60 of the cylinder body 58 for generating the vacuum within the bore 60. The vacuum plunger 46 includes a plunger cap 78, a plunger stem 80, and piston 82. The plunger cap 78 is generally planar and generally circular for improving manipulation of the vacuum plunger 46 within the bore 60 of the cylinder body 58. Similar to the handgrip 76, the plunger cap 78 is generally larger than the bore 60, while the remainder of the vacuum plunger 46 is sized to slide within the bore 60. Because of this respective size, the plunger cap 78 will abut the handgrip 76 adjacent to the bore 60 for preventing the vacuum plunger 46 from falling through the bore 60 and into the cylinder body 58.

The plunger stem 80 projects distally from the plunger cap 78 to the piston 82. The piston 82 has an annular groove 84 defining a pair of piston seals 86, 88 that circumscribe the piston 82. The piston seal 88 also projects distally to a conical point 90 for aiding alignment and insertion of the vacuum plunger 46 into the bore 60.

FIG. 3 shows a cross-section in which the vacuum pump 16 is assembled to define the flow channel 38 extending through the vacuum pump 16. More particularly, according to the exemplary embodiment, the port 44, the bore 60, the passage 63, the conduit 65, and the inlet 56 each fluidly connect and define the flow channel 38 for connecting the vacuum to the vacuum chamber 30. However, it will be appreciated that any flow channel 38 for fluidly connecting the vacuum to the vacuum chamber 30 may be used. In this respect, other embodiments may define the flow channel 38 with more or less structures.

The stopper 36 further includes a screen 92 positioned over the inlet 56 for inhibiting the mixture 14 from passing into the flow channel 38. In this respect, the screen 92 is configured for filtering the gas 12 from the mixture 14 under the influence of the vacuum so that the mixture 14 generally remains within the vacuum chamber 30. The inlet 56 also is tapered from the screen 92 to the conduit 65 in order to maximize the size of the screen 92 positioned within the inlet 56 and increase the ease with which the gas 12 may be withdrawn from the mixture 14. According to an exemplary embodiment, the screen 92 prevents the passage of particles within the mixture 14 larger than generally 37 microns. Of course, it will be appreciated that other screens may be used to prevent the passage of other sized hard particles depending on the application, type of gas 12, and type of mixture 14. In addition, some leakage of particulate and/or liquid within the mixture 14 through the screen 92 is contemplated in accordance with the invention. For example, the leakage may include foamy fluids that seep through the screen 92 during use.

While the screen 92 is positioned at the inlet 56 for inhibiting the mixture 14 from moving proximally into the flow channel 38, a first valve 94 is positioned within the flow channel 38 for generally preventing gas 12 from moving distally within the flow channel 38 toward the mixture 14. More particularly, the first valve 94 is mounted within the valve support body 62 between the passage 63 and the conduit 65. At this position, the first valve 94 is operable to open and close by the pressure differential between the passage 63 and conduit 65. In the event that proximal pressure in the passage 63 is less than a distal pressure in the conduit 65, the first valve 94 selectively opens for withdrawing gas from the conduit 65. However, in the event that the proximal pressure in the passage 63 is greater than the distal pressure in the conduit 65, the first valve 94 selectively closes for generally preventing gas from being forced into the conduit 65.

A second valve 96 is also fluidly connected to the flow channel 38 for releasing excess pressure from the flow channel 38 to an ambient environment 98. More particularly, the second valve 96 is mounted within the valve support body 62 between the passage 63 and the ambient environment 98. At this position, the second valve 96 is operable to open and close by the pressure differential between the passage 63 and ambient environment 98. In the event that proximal pressure in the passage 63 is less than an ambient pressure in the ambient environment 98, the second valve 96 selectively closes for sealing the flow channel 38 from the ambient environment 98. However, in the event that the proximal pressure in the passage 63 is greater than the ambient pressure, the second valve 96 selectively open for releasing excess pressure from the flow channel 38 to the ambient environment 98. More particularly, the second valve 96 is positioned between the flow channel 38 and a gap 100 between the vacuum pump 16 and the syringe body 19 that opens to the ambient environment 98. Thus, the second valve 96 releases excess pressure to the gap 100 for being fluidly communicated therethrough to the ambient environment 98. Particularly, exemplary embodiments of the first and second valves 94, 96 are check valves. More particularly, the first and second valves 94, 96 are umbrella check valves. However, it will be appreciated that generally any type of check valve may be used as described above. For example, the first and/or second valve 94, 96 may also be a mushroom check valve, a duckbill check valve, a ball check valve, a dome check valve, a flapper valve, or any other type of check valve for permitting one-directional flow. As such, the invention is not intended to be limited to the exemplary valves shown and described herein.

The exemplary embodiment of the invention shown in FIG. 3 generates the vacuum for withdrawing gas from the mixture 14 via the vacuum plunger 46 cooperating with the cylinder body 58. The practitioner may create the mixture 14, such as the bone graft material, using known devices and methods of mixing and then load the vacuum chamber 30 with the mixture 14 to the max fill line 28. As indicated by arrows 102a, 102b, the practitioner manipulates the plunger cap 78 to move the piston 82 back and forth within bore 60. This back and forth movement may be more particularly referred to as a vacuum stroke, indicated by arrow 102a, and a pressure stroke, indicated by arrow 102b.

During the vacuum stroke 102a, the piston 82 moves proximally, which, in turn, causes the volume of the bore 60 distal of the piston 82 to increase. The increase in volume creates a decrease in pressure, otherwise referred to herein as the vacuum. The vacuum within the bore 60 transfers to the passage 63 to simultaneously open the first valve 94 and close the second valve 96. With the first valve 94 open, the vacuum transfers through the conduit 65, inlet 56, screen 92, and throughout the fluidly connected vacuum chamber 30. The gas 12 also collects within the plurality of grooves 32 to aid in directing the gas 12 toward the inlet 56. Because the mixture 14 and gas 12 are exposed to the vacuum, the gas 12 withdraws through the screen 92 and proximally along the flow channel 38 to the increasing volume of the bore 60. However, the mixture 14 generally remains within the vacuum chamber 30 due to the screen 92, which allows the gas 12 to filter through. In the event that the mixture 14 includes a liquid and a relatively porous particulate, such as bone graft materials, the vacuum also increases the rate of absorption of the liquid within the relatively porous particulate. As such, the vacuum tends to withdraw gas 12 from the mixture 14 while also hydrating the relatively porous particulate within the mixture 14. In the case where the mixture 14 is bone graft material, reducing the gas 12 creates a more uniform mixture 14 and in less time relative to traditional methods.

The vacuum may continue to increase within the flow channel 38 so long as the piston 82 moves proximally through the vacuum stroke 102a. Once the piston 82 reaches the top of the vacuum stroke 102a, the vacuum pump 16 ceases to withdraw gas 12 from the vacuum chamber 30. As such, the pressure within the vacuum chamber 30 is below the pressure within the passage 63 causing the first valve 94 to close and generally maintain the vacuum within the vacuum chamber 30. For relatively porous mixtures 14, such as the bone graft materials, maintaining the vacuum within the vacuum chamber 30 allows gas 12 to continue to gather within the plurality of grooves 32 even while there is no vacuum being generated by the vacuum plunger 46.

Once the piston 82 is at the top of the vacuum stroke 102a, the bore 60 may be purged of gas 12 by manipulating the plunger cap 78 to move the piston 82 through the pressure stroke 102b. Through the pressure stroke 102b, the piston 82 moves distally through the bore 60, which, in turn, causes the volume of the bore 60 distal of the piston 82 to decrease. The decrease in volume creates an increase in pressure. While the first valve 94 remains closed during the increase in pressure, the second valve 96 opens when the increase in pressure raises above that of the ambient environment 98. As such, the gas 12 within the bore 60 is forced by the piston 82 from the bore 60, into the passage 63, through the second valve 96, along the gap 100, and into the ambient environment 98. The gas 12 continues to purge from the bore 60 until the piston 82 reaches the bottom of the pressure stroke 102b. The vacuum stroke 102a and pressure stroke 102b may be repeated to increase the vacuum within the vacuum chamber 30 as desired by the practitioner or as limited by the sealing capabilities of the piston 82 and/or stopper 36. According to an exemplary embodiment, the vacuum generated within the vacuum chamber 30 may be from less than approximately 0 psi to approximately −60 psi for withdrawing the gas 12 from the mixture 14 of bone graft materials.

Once the practitioner sufficiently removes the gas 12 and/or hydrates the mixture 14, the end cap 29a may be removed from the syringe body 19 to open the vacuum chamber 30 to the ambient environment 98 and release the vacuum contained therein. In this respect, the gas 12 is sufficiently removed from mixture 14 just prior to dispensing the mixture 14. To dispense the mixture 14, the practitioner then manipulates the handgrip 76 to move the vacuum plunger 46 distally within the syringe body 19, as indicated by arrow 104a. Specifically, the stopper 36 moves distal of the max fill line 28 against the mixture 14 to force the mixture 14 toward the distal opening 24. The practitioner continues to push the vacuum pump 16 through the syringe 18 until generally the entirety of the mixture 14 is ejected from the cavity 20. Of course, the practitioner may return the vacuum pump 16 to its position near the max fill line 28 or remove it from the syringe 18 altogether by moving the vacuum pump 16 proximally through the proximal opening 22, as indicated by arrow 104b. In the case of the mixture 14 including bone graft material, the bone graft material is dispensed during a medical procedure onto an anatomical site.

Figure 4A:
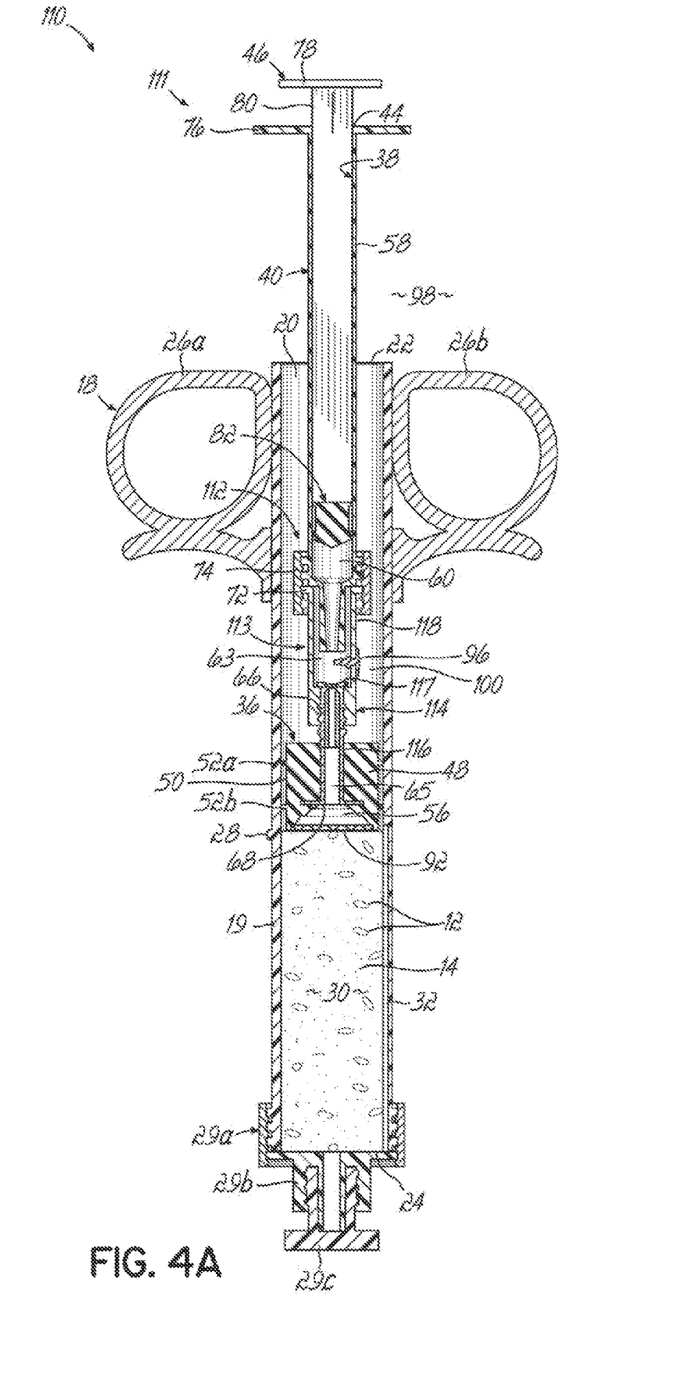
FIG. 4A is a cross-section view similar to FIG. 3, but showing another embodiment of a device for removing the gas from the mixture having a valve lock for releasing a vacuum within a vacuum chamber of the device.
Figure 4B:
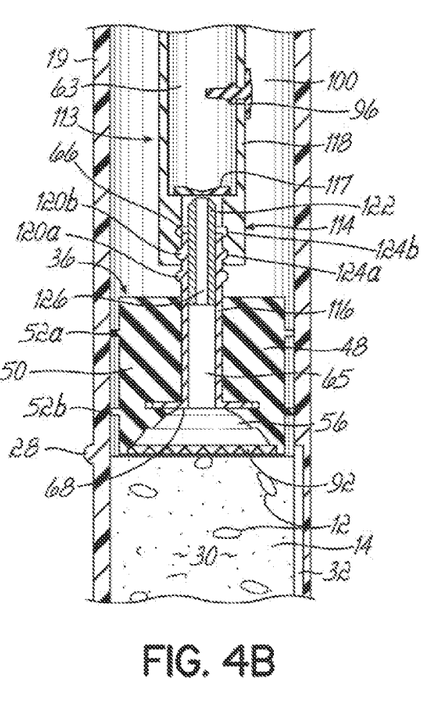
FIG. 4B is an enlarged cross-section view of FIG. 4A showing the valve lock of FIG. 4A in an operational position.
Figure 4C:
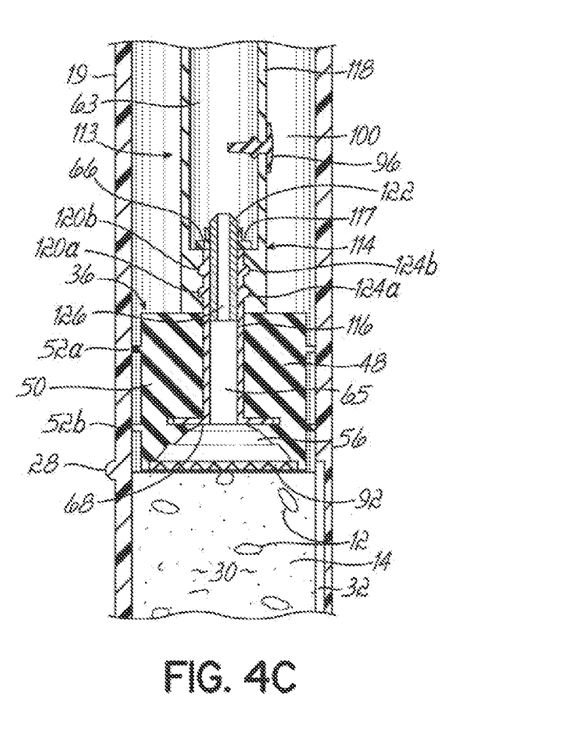
FIG. 4C is a cross-section view similar to FIG. 4B, but showing the valve lock in a locked open position.

With respect to FIGS. 4A, 4B, and 4C, another embodiment of a device 110 includes a vacuum pump 111. The vacuum pump 111 has a pump body 112 with a distal portion 113. The vacuum pump 111 has a distal portion 113 with a valve lock 114 for releasing the vacuum within the vacuum chamber 30 without the need to remove the end cap 29a. Accordingly, similar numbers refer to similar features described above. The valve lock 114 includes a lock stem 116 that cooperates with a valve lock support body 118 for selectively opening a first valve 117 at the discretion of the practitioner. The lock stem 116 includes the proximal end 66, the distal lip 68, and the conduit 65. In addition, the lock stem 116 also includes distal and proximal annular detents 120a, 120b and a push tube 122. The distal and proximal annular detents 120a, 120b are positioned about the lock stem 116 and adjacent to the proximal end 66. Furthermore, the valve lock support body 118 includes the first valve 117, the passage 63, and distal and proximal annular grooves 124a, 124b for selectively receiving the distal and proximal annular detents 120a, 120b. In this way, the push tube 122 is positioned adjacent to the first valve 117. The exemplary embodiment of the first valve 117 shown in FIGS. 4A, 4B, and 4C is a dome check valve that may be forced open by the push tube 122. However, any valve that may cooperate with the valve lock 114 may be similarly used.

On one hand, FIG. 4B shows the valve lock 114 in an operational position such that the first valve 117 operates as described above. Specifically, the proximal annular detent 120b is selectively positioned within the distal annular groove 124a so that the push tube 122 does not impede the opening and closing of the first valve 117. In fact, the push tube 122 has a lumen 126 extending therethrough for fluidly connecting the passage 63 and the conduit 65 when the first valve 117 is open.

On the other hand, FIG. 4C shows the valve lock 114 in a locked open position such that the push tube 122 extends through the first valve 117. Specifically, the distal and proximal annular detents 120a, 120b are selectively positioned within the distal and proximal annular grooves 124a, 124b, respectively, so that the push tube 122 actuates the first valve 117. Because the lumen 126 fluidly connects the passage 63 to the conduit 65 and maintains the flow channel 38 as open, the vacuum being contained within the vacuum chamber 30 is released to the remaining flow channel 38. Moreover, the vacuum plunger 46 may be removed from the bore 60 to release the remaining vacuum within the flow channel 38 to the ambient environment 98.

During use, the practitioner may be interested in using the valve lock 114 as described above for reducing the vacuum within the vacuum chamber 30. Furthermore, leakage from the mixture 14 may seep through the screen 92 and into the flow channel 38, while removing gas 12 from the mixture 14. While some leakage may not damage or reduce the effectiveness of the device 110, it may be possible for too much leakage to collect within either one or both of the first and second valves 117, 96. Too much leakage may eventually seize the first or second valves 117, 96 partially open or partially closed, leading to reduced vacuum within the vacuum chamber 30. However, by operating the valve lock 114 to actuate the first valve 117, the sudden inflow of gas 12 may effectively break up collected leakage and withdraw it back into the vacuum chamber 30 with the mixture 14. As such, operating the valve lock 114 may improve cleanliness and reduce the likelihood of seizing one or both of the first and second valves 117, 96.

According to the exemplary embodiment, the valve lock 114 effectively "snaps" between the distal and proximal detents 120a, 120b. However, it will be appreciated that the valve lock 114 may effectively move between the operational position and the locked open position via cooperating threads. In such an instance, the lock stem 116 may be rotated relative to the valve lock support body 118 to move the distally or proximally. For example, the lock stem 116 may rotate approximately 90 degrees between the operational position and the locked position. Similarly, the lock stem 116 may rotate approximately 180 degrees between the operational position and the locked position. In this respect, any valve lock 114 for operation with the first or second valves 117, 96 may be used as described above.

Figure 5:
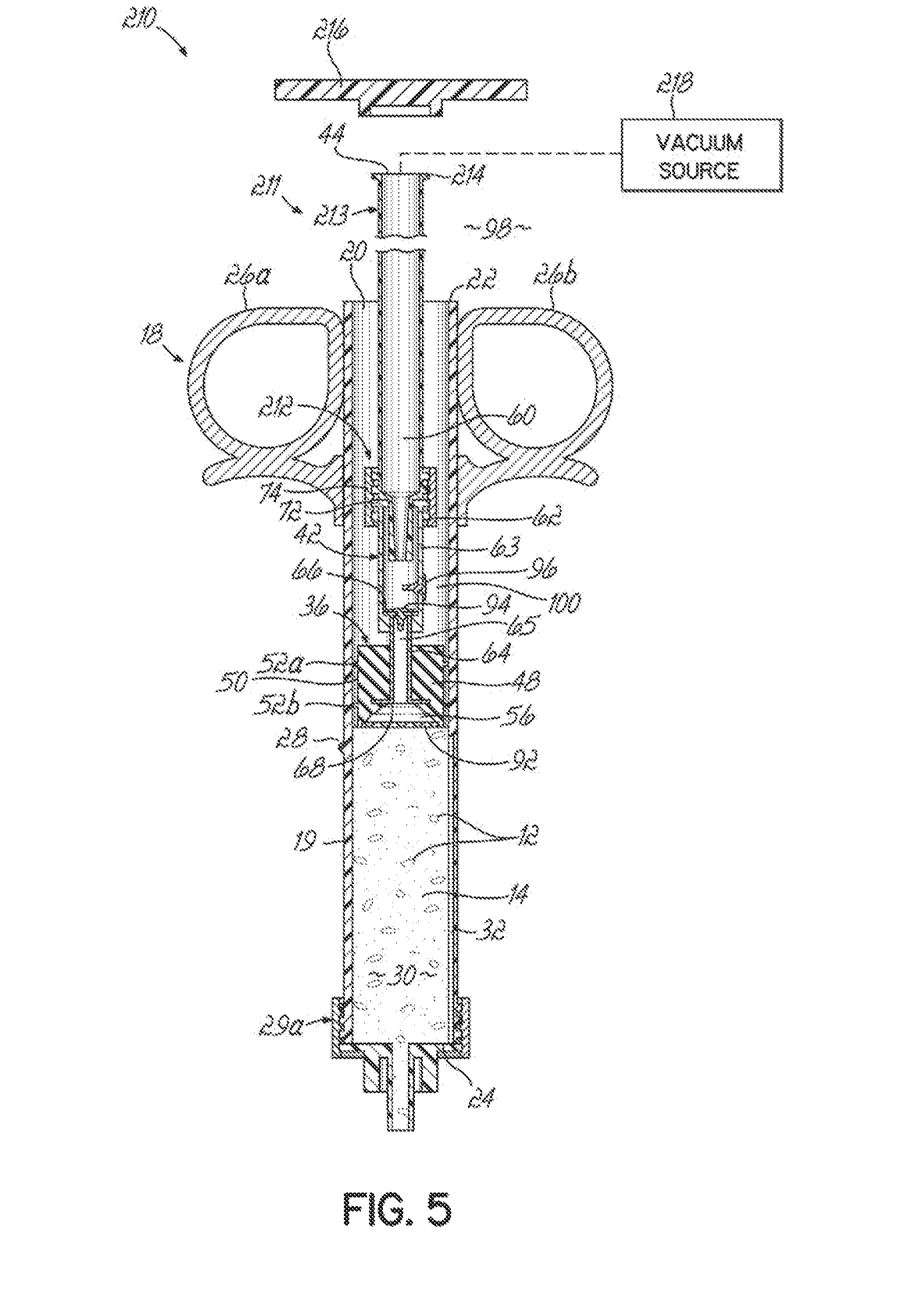
FIG. 5 is a cross-section view similar to FIGS. 3 and 4A but showing another embodiment of a device for removing the gas from the mixture configured for operatively connecting to a vacuum source.

With respect to FIG. 5, yet another embodiment of the device 210 includes a vacuum pump 211. The vacuum pump 211 has a pump body 212 with a proximal portion 213. The proximal portion 213 of the pump body 212 includes the bore 60 extending therethrough. Accordingly, similar numbers refer to similar features described above. The pump body 212 also includes a proximal pump body end 214 and a removable plunger cap 216. The removable plunger cap 216 is removably connected to the proximal pump body end 214 adjacent to the port 44. More particularly, the removable plunger cap 216 of the exemplary embodiment, is generally circular, planar, and threaded onto the proximal pump body end 214. While connected to the proximal pump body end 214, the removable plunger cap 216 is positioned along the pump body 212 for improving manipulation of the vacuum pump 211 during use. As such, the removable plunger cap 216 is generally larger than the cavity 20 of the syringe body 19, while the remainder of the vacuum pump 211 distal from the removable plunger cap 216 is sized for insertion within the syringe body 19. Because of this respective size, the removable plunger cap 216 will abut the syringe body 19 adjacent to the proximal opening 22 for preventing the vacuum pump 211 from falling through the distal opening 24 of the syringe body 19.

However, the removable plunger cap 216 may also be removed so that the port 44 may be operatively connected to a vacuum device, which, according to the exemplary embodiment, is a vacuum supply 218. The vacuum supply 218 may be any supplied vacuum. For example, a medical or surgical environment may be fitted with the vacuum supply 218 to operatively connect to the port 44. In this respect, the device 210 is similar to the device 10 shown in FIGS. 3 and 4A, and it will be appreciated that many of the same features may be interchangeable. For instance, the device 210 may also be fitted with the valve lock 114 (see FIG. 4A) to achieve performance similar to that described above in a previous embodiment.

Figure 6:
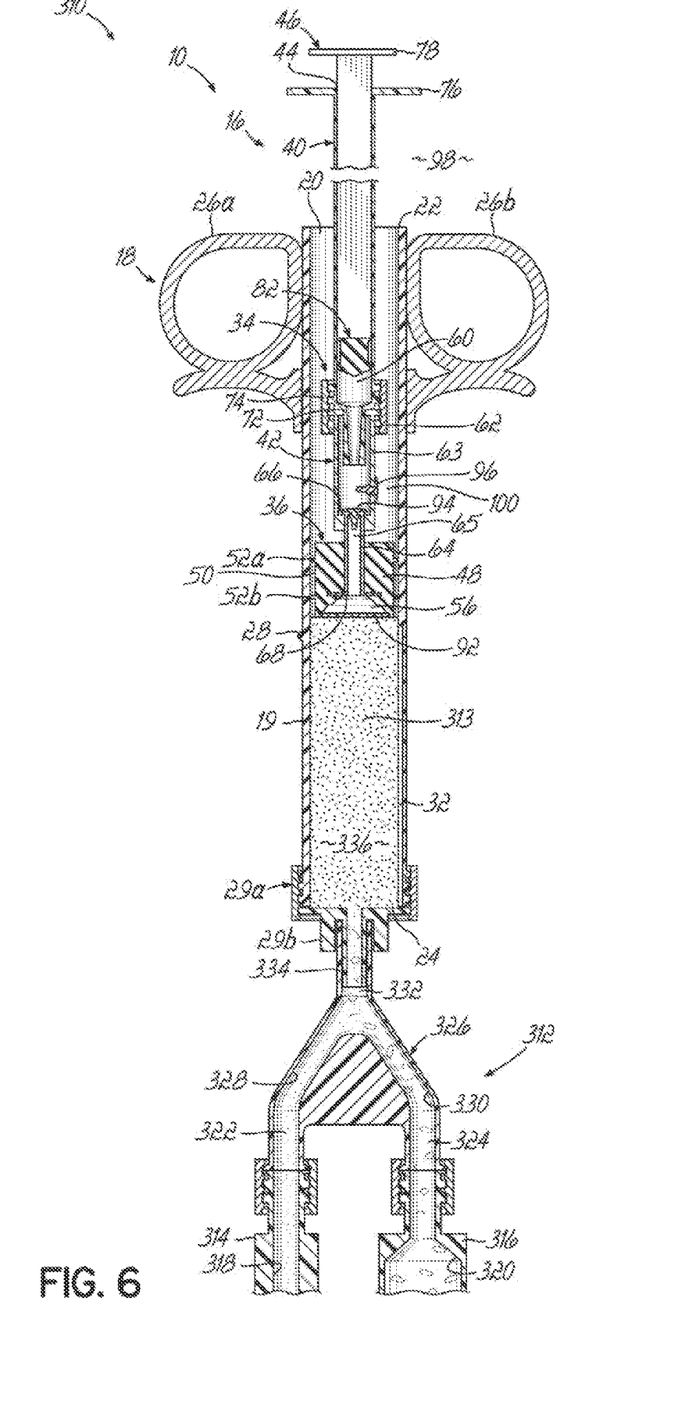
FIG. 6 is a cross-section of an apparatus including the device shown in FIG. 3 and a fluid source syringe for removing the gas from a dry particulate.
Figure 7:
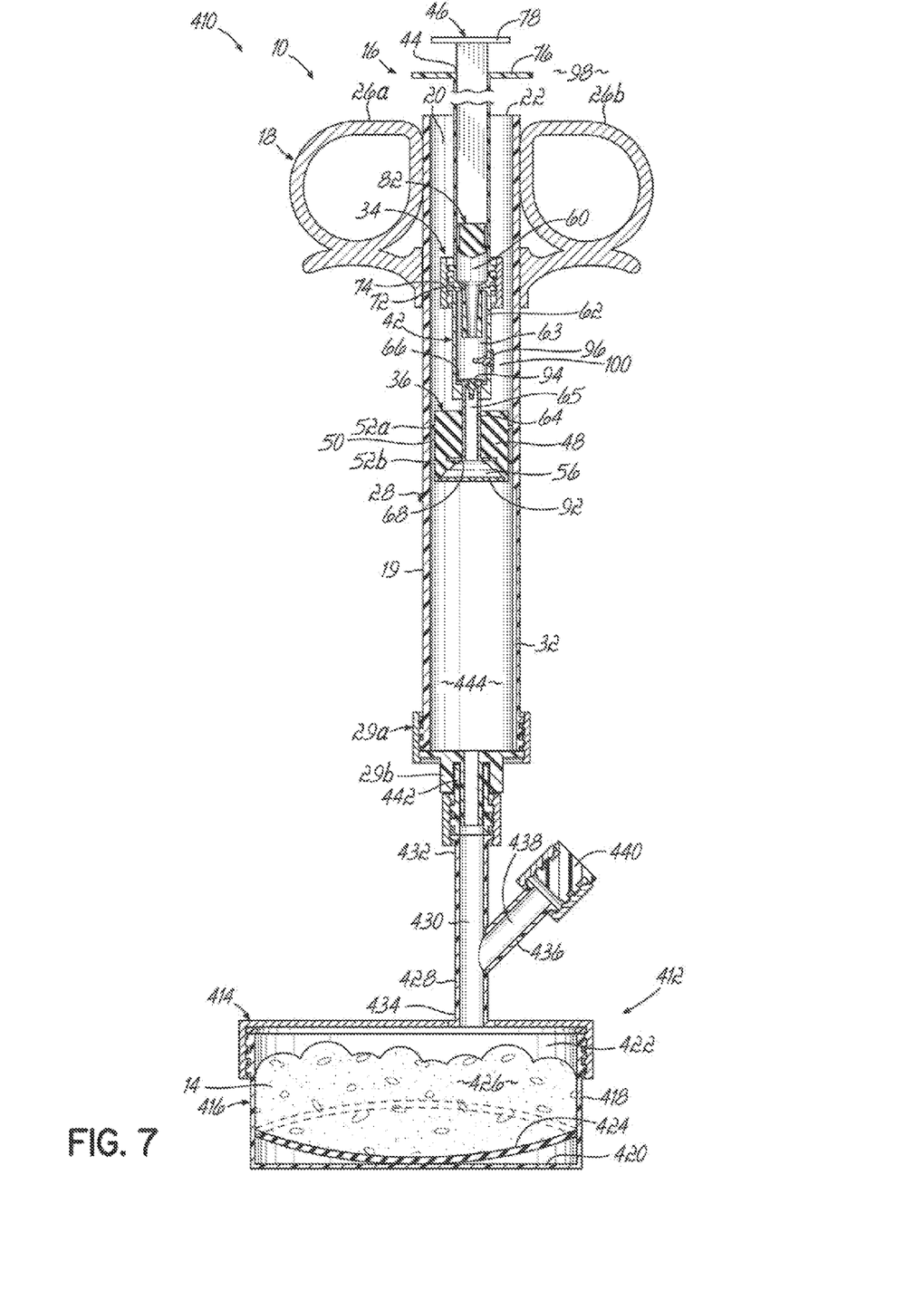
FIG. 7 is a cross-section of another apparatus including the device shown in FIG. 3 and a mix container for removing the gas from the mixture of bone graft material.

FIG. 6 and FIG. 7 show various apparatuses for creating the mixture 14 (see FIG. 1) with like numbers indicating like features described above. With respect to FIG. 6, an apparatus 310 includes the device 10 fluidly connected to a mixture source, such as a fluid source syringe 312 of an exemplary embodiment. A dry particulate 313 is shown within the cavity 20 of the syringe 18 between the vacuum pump 16 and the end cap 29a. According to an exemplary embodiment, the dry particulate 313 is preloaded within the cavity 20 and may be included within the device 10 for future use. However, in the alternative, the practitioner may also remove the end cap 29a, load dry particulate 313 through the distal opening 24, and replace the end cap 29a during use.

The fluid source syringe 312 contains at least one liquid for mixing with the dry particulate 313 to form the mixture 14 (see FIG. 1). An exemplary embodiment of the fluid source syringe 312 includes first and second syringe housings 314, 316 that each respectively define first and second syringe chambers 318, 320. The first and second syringe chambers 318, 320 each contain respective first and second liquids 322, 324 and are variable in size so that each may selectively decrease or increase in volume. Furthermore, the fluid source syringe 312 includes an adapter 326 which defines a first channel 328 and a second channel 330 that join together into a primary channel 332. As such, the first and second channels 328, 330 are fluidly connected to the first and second syringe chambers 318, 320 and the primary channel 332 is configured for fluid attachment to the end cap 29a.

As shown in FIG. 6, the female luer cap 29c (see FIG. 3) is removed from the end cap 29a so that the male luer coupling 29b is fluidly connected to a female luer coupling 334 of the primary channel 332. Once fluidly connected, a dual vacuum chamber 336 is defined by the vacuum chamber 30, as described above, and also by the primary channel 332, the first channel 328, the second channel 330, the first syringe chamber 318, and the second syringe chamber 320.

In use, the device 10 withdraws gas from the dual vacuum chamber 336 similar to the vacuum chamber 30 shown in FIG. 3 and described above. However, because the first and second syringe chamber 318, 320 selectively vary by volume, the vacuum compresses each of the chambers 318, 320 simultaneously. In this way, the first and second liquids 322, 324 are simultaneously forced toward the dry particulate mix 313. The practitioner may continue withdrawing the gas 12 from the dual vacuum chamber 336 until the dry particulate 313 is sufficiently hydrated with the first and second liquids 322, 324 to form the mixture 14 described above with respect to FIG. 3.

With respect to FIG. 7, another apparatus 410 includes the device 10 fluidly connected to another mixture source, such as a mix container 412. The mix container 412 generally includes a lid 414 removably attached to a base 416. The base 416 further includes an annular sidewall 418 surrounding a bottom 420 and defines a mix cavity 422 for receiving the mixture 14. Within the mix cavity 422, a diaphragm 424 is movably positioned against the annular sidewall 418 and extends generally across the bottom 420. More particularly, the diaphragm 424 is fluidly sealed against the annular sidewall 418 and may move proximally toward the lid 414 as indicated in FIG. 7. In this respect, the diaphragm 424, the lid 414, and the sidewall 418 collectively define a mix volume 426. Because the diaphragm 424 is movable relative to the base 416 and the lid 414, the mix volume 426 may increase or decrease depending on the pressure within the mix volume 426.

The lid 414 includes a primary tube 428 having a primary mix channel 430 extending therethrough. The primary tube 428 also has a proximal tube portion 432 and a distal tube portion 434. The proximal tube portion 432 is configured for fluidly connecting to the device 10, and the distal tube portion 434 is attached to the lid 414 so that the primary mix channel 430 is fluidly connected to the mix volume 426. According to the exemplary embodiment, the primary tube 428 also has a secondary tube 436 extending therefrom. The secondary tube 436 defines a secondary mix channel 438 fluidly connected to the primary mix channel 430. In this way, the practitioner may have improved access within the mixing container 412, even when connected to the device 10. As shown, the secondary mix channel 438 is blocked with a threaded plug 440 for fluidly sealing the secondary mix channel 438 from the ambient environment 98.

As shown in FIG. 7, the female luer cap 29c (see FIG. 3) is removed from the end cap 29a so that the male luer coupling 29b is fluidly connected to a female luer coupling 442 of the primary mix channel 430. Once fluidly connected, a mix vacuum chamber 444 is defined by the vacuum chamber 30, as described above, and also by the primary mix channel 430, the second mix channel 438, and the mix volume 426.

In use, the device 10 withdraws gas from the mix volume 426 similar to the vacuum chamber 30 shown in FIG. 3 and described above. However, because the mix volume 426 selectively varies under the influence of pressure, the vacuum compresses the mix volume 426 toward the lid 414. In this way, the mixture 14 is forced from the mixing container 412 and to the device 10. According to an exemplary embodiment, the practitioner may create the mixture 14 and load it within the mix volume 426 for use. Alternatively, the mixing container 412 may include dry particulate 313 similar to that of FIG. 6 with one or both first and second liquids being added to the mix volume 426 through the second mix channel 428 for use by the practitioner.

While the present invention has been illustrated by the description of one or more embodiments thereof, and while the embodiments have been described in considerable detail, they are not intended to restrict or in any way limit the scope of the appended claims to such detail. The various features shown and described herein may be used alone or in any combination. Additional advantages and modifications will readily appear to those skilled in the art. The invention in its broader aspects is therefore not limited to the specific details, representative apparatus and method and illustrative examples shown and described. Accordingly, departures may be from such details without departing from the scope of the general inventive concept.

What is claimed is:

1. A method of removing a gas from a mixture of biomaterials within a syringe, the syringe having a cavity with a vacuum pump positioned therein, the vacuum pump and the syringe at least partially defining a vacuum chamber, the vacuum pump comprising a pump body operatively connected to a stopper, a flow channel extending through the pump body and the stopper, the method comprising;
   generating a vacuum through the flow channel in fluid communication with the vacuum chamber; and
   withdrawing the gas through the flow channel within the stopper and removing the gas from the mixture of biomaterials within the vacuum chamber.

2. The method of claim 1 wherein the biomaterials further comprise bone graft materials.

3. The method of claim 2 further comprising removing the gas from the mixture of bone graft materials just prior to dispensing the mixture of the bone graft materials onto an anatomical site during a medical procedure.

4. The method of claim 1 further comprising filtering the gas from the mixture of biomaterials through a screen covering the flow channel within the stopper.

5. The method of claim 1 further comprising:
   manipulating the pump body to move the operatively connected plunger through the cavity; and
   ejecting the mixture of biomaterials from the cavity with the moving plunger.

6. The method of claim 1 further comprising opening a valve to fluidly connect the flow channel to the vacuum chamber.

7. The method of claim 1 wherein the mixture of biomaterials includes a particulate and a liquid, the method further comprising hydrating the particulate with the liquid by withdrawing the gas from the vacuum chamber.

* * * * *